(12) United States Patent
Wang

(10) Patent No.: US 8,805,535 B2
(45) Date of Patent: Aug. 12, 2014

(54) MRI-COMPATIBLE IMPLANTABLE MEDICAL LEAD

(75) Inventor: Michael Wang, Uppsala (SE)

(73) Assignee: St. Jude Medical AB, Jarfalla (SE)

( * ) Notice: Subject to any disclaimer, the term of this patent is extended or adjusted under 35 U.S.C. 154(b) by 72 days.

(21) Appl. No.: 13/504,118

(22) PCT Filed: Oct. 7, 2010

(86) PCT No.: PCT/EP2010/065028
§ 371 (c)(1),
(2), (4) Date: Apr. 25, 2012

(87) PCT Pub. No.: WO2011/051094
PCT Pub. Date: May 5, 2011

(65) Prior Publication Data
US 2012/0221086 A1    Aug. 30, 2012

(30) Foreign Application Priority Data
Oct. 30, 2009  (WO) ................. PCT/SE2009/000479

(51) Int. Cl.
*A61N 1/04*    (2006.01)

(52) U.S. Cl.
USPC ............................................ 607/116; 607/63

(58) Field of Classification Search
USPC .................................................. 607/63, 116
See application file for complete search history.

(56) References Cited

U.S. PATENT DOCUMENTS

| | | | |
|---|---|---|---|
| 5,519,235 A * | 5/1996 | Ramesh ......................... 257/295 |
| 2005/0222657 A1 * | 10/2005 | Wahlstrand et al. .......... 607/116 |
| 2006/0252314 A1 | 11/2006 | Atalar et al. |
| 2008/0033497 A1 | 2/2008 | Bulkes et al. |
| 2008/0129435 A1 | 6/2008 | Gray |
| 2008/0243218 A1 | 10/2008 | Bottomley et al. |
| 2009/0171421 A1 * | 7/2009 | Atalar et al. ..................... 607/63 |
| 2010/0114281 A1 | 5/2010 | Swoyer et al. |

OTHER PUBLICATIONS

International Search Report—Int'l App. No. PCT/EP2010/065028; Int'l Filing Date: Oct. 7, 2010.
Written Opinion of the Int'l Searching Authority—Int'l App. No. PCT/EP2010/065028; Int'l Filing Date: Oct. 7, 2010.

* cited by examiner

*Primary Examiner* — Eric D. Bertram

(57) ABSTRACT

An MRI-compatible implantable medical lead includes two electrodes coupled to a distal end of the lead, two matching electrode terminals coupled to a proximal end and a lead body in the form of an outer insulating tubing running from the distal end to the proximal end. A coaxial conductor assembly is arranged in a bore of the outer insulating tubing and comprises an inner conductor, an outer conductor and an inner insulating tubing arranged between the inner and outer conductors. A capacitor is arranged between the inner conductor and the outer conductor at a distance from the distal end defined based on the magnetic field strength of the MRI system with which the lead is compatible.

14 Claims, 5 Drawing Sheets

MRI-COMPATIBLE IMPLANTABLE MEDICAL LEAD

CROSS REFERENCE TO RELATED APPLICATION(S)

This is a U.S. national stage application of International Application No. PCT/EP2010/065028, filed on Oct. 7, 2010, which claims priority to International Application No. PCT/SE2009/000479, filed on Oct. 30, 2009, the content of which is incorporated herein by reference.

TECHNICAL FIELD

The present invention generally relates to implantable medical leads and in particular to MRI-compatible implantable medical leads.

BACKGROUND

Magnetic Resonance Imaging (MRI) is of great use for generating an image of the internal tissues of a human body. However, for persons who have an implantable medical lead implanted in their body, there are problems with induced currents in the implantable medical lead causing, in turn, heating of the lead, in particular at the distal tip of the lead. MRI is based on Nuclear Magnetic Resonance (NMR) for protons of hydrogen nuclei. It is well-known that all nuclei have spin which are randomly oriented. When a magnetic field is applied, the proton spins become either parallel or anti-parallel, and the energy levels are split into a higher level for the anti-parallel spin and a lower level for the parallel spin. The difference in energy between the two states is proportional to the magnetic field. Furthermore, the protons start precessing around the magnetic field direction with a precession frequency (Larmor frequency) which is proportional to the magnetic field, and with a precession angle, which is also called flip angle and is defined as the angle between the precession axis and the direction of the magnetic field. This precession angle in fact reflects the ratio between the energy levels. If an external pulsed radio frequency (RF) signal with Larmor frequency is applied, a few protons from the lower energy level with parallel spin will be excited to the higher energy level. This implies that the precession angle will change and the protons will precess in phase. The RF pulse width is typically of a few ms and is generally chosen for a time duration at which all protons are guaranteed to precess in phase. After some time (in the order of ms) these protons start to relax, that is the protons excited to the higher anti-parallel spin level will fall back to the lower parallel spin level, which implies that the precession angle falls back to the original value, and at the same time these protons will also de-phase. Both these processes will proceed with slightly different time constants, generally in the order of hundreds of ms.

A homogeneous medium can be easily identified by measuring the two time constants using this nuclear magnetic resonance (NMR) method. For an inhomogeneous medium, such as a human body, however, a gradient magnetic field is added on top of the static magnetic field to make every volume element unique. Along with accurate timing, the two time constants of the volume elements can be extracted and the individual volume element properties can be identified. This imaging method using the NMR principle is known as MRI.

In vitro MRI experiments have shown that an implantable medical lead acts like an antenna since the effective length of the lead is close to a multiple of the RF wavelength and thereby receives the pulsed RF signal of the MRI scanning equipment. The reception of the RF energy results in an RF wave propagating along the lead and heating the lead tip to an unacceptable level. Some other parts of the lead become heated as well, although not as much as the tip.

Referring to an in vitro set up, where a particular gel is used to simulate human tissue, the mechanisms for the RF energy transfer are identified as follows. As mentioned above, the precession frequency is proportional to the magnetic field, and more particularly 42.58 MHz/Tesla. Currently most MRI devices and systems operate at 1.5 Tesla (T), while 3 T MRI devices are expected to increase in the future. Thus, the frequency of the RF pulses, or RF wave, produced in a 1.5 T MRI device is about 64 MHz. The RF wave first passes through the boundary between the air and the gel. The RF wave undergoes a speed reduction from the speed in air $v_0$ to a speed in the gel (human body) $v_1$ due to the dielectric constant ($\in$) of the gel, where $$v_1 = \frac{v_0}{\sqrt{\varepsilon}}.$$

The wavelength $\lambda$ is also reduced by the same factor, i.e.

$$\lambda_1 = \frac{\lambda_0}{\sqrt{\varepsilon}},$$

where $\lambda_0$ is the wavelength in air and $\lambda_1$ denotes the wavelength in the gel (human body). The dielectric constant of the human tissue on average is in such an order that the resulting wavelength in human tissue becomes close to the physical length of a typical implantable medical lead, e.g. in the order of half a meter. This transforms the lead to a good antenna. The RF energy is picked up by the outer conductor coil of the lead, and is then transferred to the inner conductor coil via the inter-coil capacitance. This coaxial structure of the lead in fact forms a transmission line, and the potential difference along the lead and between the outer and inner conductor coils cause the above-mentioned propagation. The RF energy is eventually transferred to the lead tip, causing heating of the tip.

This problem of lead tip heating has been addressed in the prior art, such as in US 2008/0033497 A1, where different solutions have been suggested. According to one solution, the inner and outer conductor coils are wound in opposite directions and they are interconnected at their ends. The purpose is to reduce the total current. According to another solution, RF blocking circuits are inserted. According to yet another solution the conductor coils are arranged so as to create resonance circuits.

WO 2007/047966 also aims at providing a solution to the problem of tip heating, however in a lead structure where the conductors are not provided in a coaxial structure with inner and outer conductor coils but arranged in parallel. Either the conductors are straight and parallel, individually and partially wound and parallel, or co-wound while still parallel. Capacitors are arranged to interconnect the conductors. The capacitors are arranged at regular or irregular distances from each other. By means of the capacitances a high impedance circuit is obtained, which, when appropriately tuned, reduces the coupling of the pulsed RF signal to the lead.

There is still a need for an implantable medical lead that is compatible with MRI systems, and in particular such an implantable medical lead that can be easily manufactured.

SUMMARY

Briefly, an implantable medical lead is compatible with an MRI system. The implantable medical lead comprises a first electrode and a second electrode arranged in connection with a distal end. A first electrode terminal and a second electrode terminal are arranged in connection with an opposite, proximal end of the implantable medical lead. This proximal end is configured to be mechanically and electrically connected to an implantable medical device. A lead body comprises an outer insulating tubing running from the distal end to the proximal end and has a bore that houses a coaxial conductor assembly. The coaxial conductor assembly comprises an inner conductor electrically connected to the first electrode and the first electrode terminal, an outer conductor electrically connected to the second electrode and the second electrode terminal and an inner insulating tubing arranged between the conductors and electrically isolating the conductors from each other. The MRI-compatibility is achieved by arranging a capacitor between the inner conductor and the outer conductor at a defined distance from the distal end. This distance is furthermore defined based on the magnetic field strength of the MRI system.

Defining this distance where the capacitor is arranged based on the magnetic field strength of the MRI system achieves the MRI-compatibility by utilizing impedance transformation properties of the coaxial structure of the implantable medical lead. Thus, the impedance of the capacitor will, due to the impedance transformation at this particular position on the implantable medical lead relative the distal end, mirror the impedance towards the distal end to provide a low impedance between the first and second electrodes. Hence, any current that will be induced due to the MRI system will be drained inside the implantable medical lead and any tissue heating will be significantly reduced.

BRIEF DESCRIPTION OF THE DRAWINGS

The invention, together with further objects and advantages thereof, may best be understood by making reference to the following description taken together with the accompanying drawings, in which.

DETAILED DESCRIPTION

Throughout the drawings, the same reference numbers are used for similar or corresponding elements.

The present embodiments generally relate to an implantable medical lead and in particular to such an implantable medical lead that is suitable for implantation in an animal subject, preferably a mammalian subject and more preferably a human subject. The implantable medical lead can additionally be used in subjects exposed to an MRI system or scanner and is therefore MRI-compatible.

MRI-compatible as used herein implies that any heating of electrodes in connection with the distal end of the implantable medical lead caused by a current induced by RF fields of the MRI system is at an acceptable level to thereby not cause or at least reduce the risk of causing significant injuries to surrounding tissue in the subject body or damages to internal lead parts.

Figure 1:
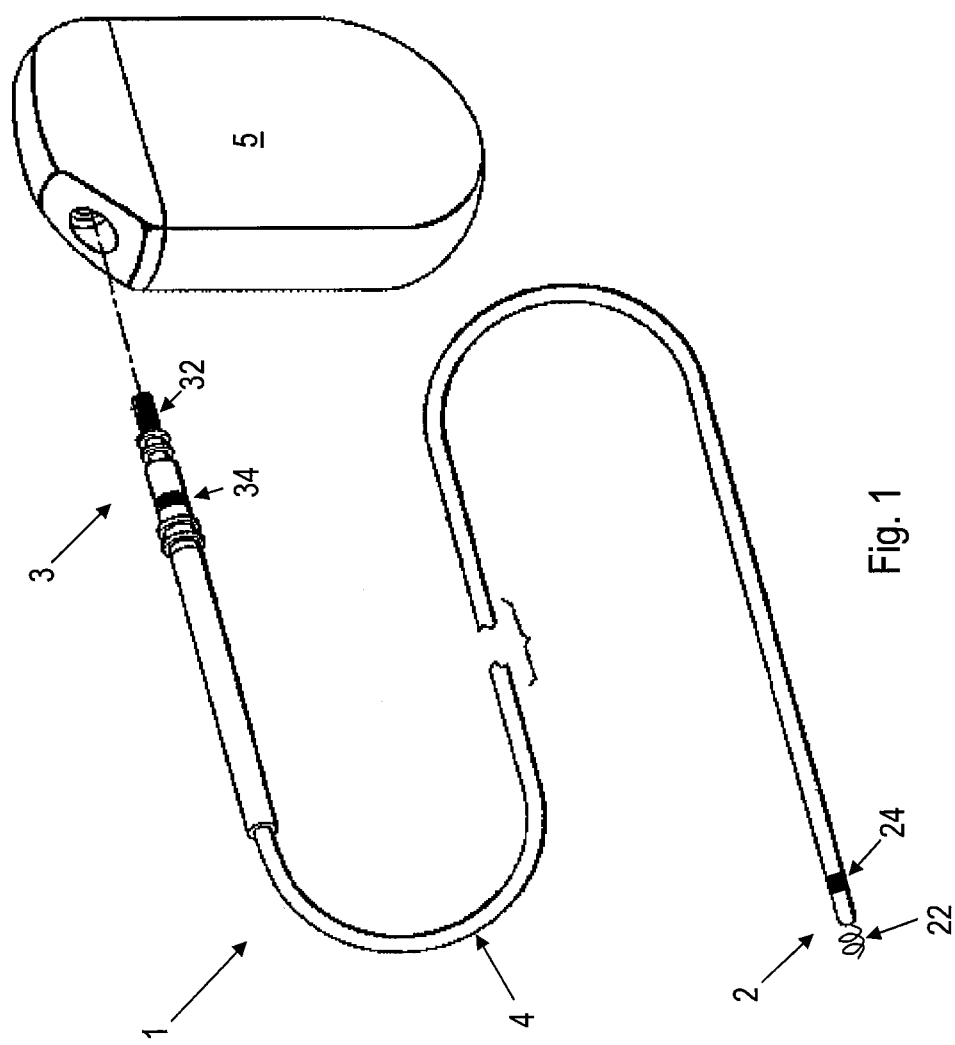
FIG. 1 is an overview of an MRI-compatible implantable medical lead according to an embodiment.

FIG. 1 is a schematic overview of an implantable medical lead 1 according to an embodiment. The implantable medical lead 1 comprises a distal end 2 designed to be introduced into a suitable pacing site to enable delivery of pacing pulses and sensing electric activity of the tissue, such as heart, at the particular pacing site. At least a first electrode 22 and a second electrode 24, generally denoted pacing and sensing electrodes in the art, are arranged in connection with the distal end 2. It is these electrodes 22, 24 that deliver pacing pulses to the tissue and captures electric signals originating from the tissue. The implantable medical lead 1 comprises multiple, i.e. at least two, electrodes 22, 24 in connection with the distal end 2. In FIG. 1, a so-called bipolar implantable medical lead 1 has been illustrated having two electrodes 22, 24. This should merely be seen as an illustrative example and the implantable medical lead 1 could instead be a tripolar lead with three electrodes, a quadropolar lead with four electrodes or indeed have five of more electrodes.

In FIG. 1, one of the electrodes is exemplified as an active fixation electrode 22 in the form of a helix. This electrode 22 thereby not only operates as a pacing and sensing electrode but is also employed for anchoring the implantable medical lead 1 to a tissue in the subject body by being screwed into the tissue, which is well known in the art. In an alternative approach, the first electrode 22 is not an active fixation electrode but could instead be a tip electrode or a ring electrode present in connection with the distal end 2 of the implantable medical lead 1. The second electrode 24 of the implantable medical lead 1 has been exemplified as a ring electrode 24 provided at some distance from the first electrode 22 towards an opposite, proximal end 3 of the implantable medical lead 1.

The proximal end 3 of the implantable medical lead 1 is configured to be mechanically and electrically connected to an implantable medical device (IMD) 5. The IMD 5 can be any implantable medical device used in the art for generating and applying, through the implantable medical lead 1, electric pulses and/or shocks to tissues. The IMD 5 is advantageously a pacemaker, defibrillator or cardioverter to thereby have the implantable medical lead 1 implanted in or in connection to a ventricle or atrium of the heart. However, also other types of IMDs 5 that are not designed for cardiac applications, such as neurological stimulator, physical signal recorders, etc. can be used as IMDs 5 to which the implantable medical lead 1 can be connected.

The proximal end 3 comprises at least a first and a second electrode terminal 32, 34 that provide the electric interface of the implantable medical lead 1 towards the IMD 5. Thus, each electrode terminal 32, 34 is connected to a respective connector terminal in the IMD 5 to thereby provide electric connection between the IMD 5 and the electrodes 22, 24 through the electrode terminals 32, 34 and a coaxial conductor assembly, to be further described herein.

The implantable medical lead 1 typically comprises a respective electrode terminal 32, 34 for each electrode 22, 24 in connection with the distal end 2.

Figure 2:
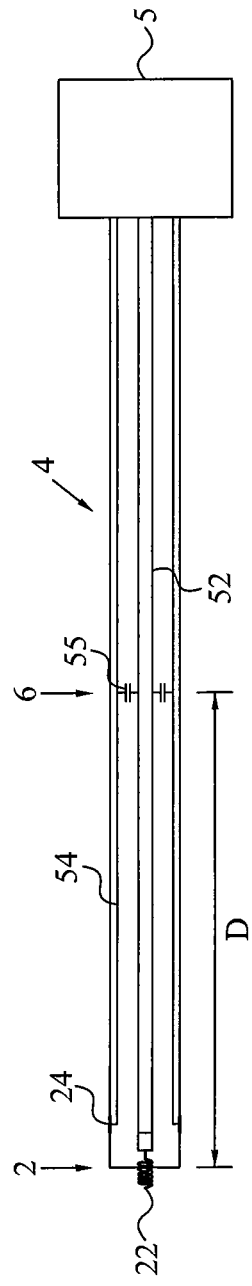
FIG. 2 is a simplified cross-sectional view of an MRI-compatible implantable medical lead according to an embodiment.
Figure 5:
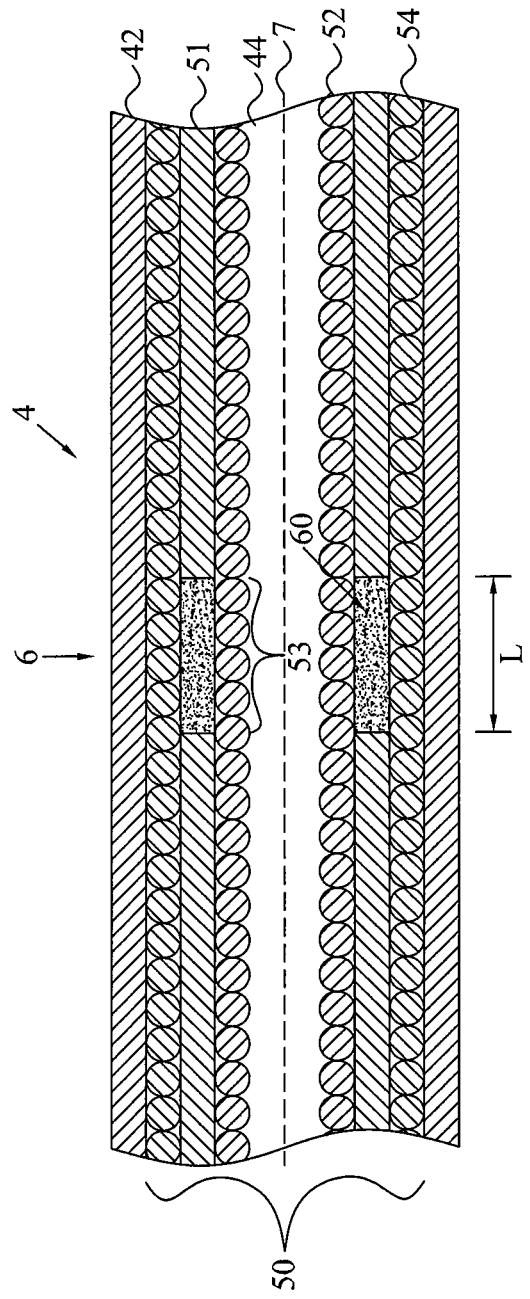
FIG. 5 is a cross-sectional view of portion of the lead body of an MRI-compatible implantable medical lead according to an embodiment.

The implantable medical lead 1 also comprises a lead body 4 running from the proximal end 3 to the distal end 2. This lead body 4 comprises an insulating tubing 42 having a bore 44 (see FIG. 5). This bore 44 is designed and dimensioned to house a coaxial conductor assembly 50 that provides the electrical connection between the multiple electrodes 22, 24 and the multiple electrode terminals 32, 34. The coaxial conductor assembly 50 comprises, as is best seen in FIGS. 2 and 5, an inner conductor 52 that is electrically connected to the first electrode 22 and the first electrode terminal 32. This inner conductor 52 is preferably in the form of an inner conductor coil 52 of an electrically conducting, typically metal, material. The coaxial conductor assembly 50 further comprises an outer conductor 54 coaxially arranged relative the inner conductor 52. The outer conductor 54 is electrically connected to the second electrode 24 and the second electrode terminal 34. This outer conductor 54 is preferably also coiled and thereby provided in the form of an outer conductor coil 54. In such a case, the inner conductor 52 is coaxially arranged in a bore or channel formed by the outer conductor coil 54. The outer conductor 54 is also made of an electrically conducting, typical metal, material.

An inner insulating tubing 51 is arranged between the inner conductor 52 and the outer conductor 54 for electrically isolating the inner conductor 52 from the outer conductor 54. In such a case, the inner conductor 52 is preferably coaxially arranged in a bore or channel of the inner insulating tubing 51. The inner insulating tubing 51 and the inner conductor 52 are also coaxially arranged in the bore or channel of the outer conductor 54 to thereby form the coaxial conductor assembly 50.

Though the inner and outer conductors 52, 54 are preferably in the form of respective conductor coils the embodiments are not limited thereto. In an alternative approach the inner conductor 52 could be in the form of an electrically conducting cable or wire running in the bore of the inner insulating tubing 51. The outer conductor 54 could then be in the form of a coiled conductor or some other conductor structure as long as the two conductors 52, 54 are coaxially arranged.

According to the embodiments, the implantable medical lead 1 is designed to be MRI-compatible through the inclusion of a capacitor 55 arranged between the inner conductor 52 and the outer conductor 54. This capacitor 55 is furthermore positioned in the implantable medical lead 1 at a distance D from the distal end 2. According to the embodiments, this distance D is defined based on the magnetic field strength of the MRI system, with which the implantable medical lead 1 is compatible.

The pulsed RF wave from the MRI scanning equipment comprises an electric and a magnetic field component which are 90 degrees out of phase. In vitro MRI experiments have shown that an implantable medical lead 1 acts like an effective antenna since the electrical length of the implantable medical lead 1 is close to the RF effective wavelength in the medium (or a multiple thereof) and thereby effectively absorbs the energy of the pulsed RF signal of the MRI scanning equipment. The incident RF wave interacts with the outer conductor coil 54, depositing part of its energy with propagation phase to the outer conductor coil 54, thereby inducing an axial electromagnetic wave traveling along the implantable medical lead 1, which is literally a transmission line. In more detail, the incident RF wave interacts with the outer conductor coil 54 inducing potential difference between the outer conductor coil 54 and inner conductor coil 52, which in turn creates a radial electric field along the implantable medical lead 1. The potential variation along the inner and outer conductor coils 52, 54 also causes a current flowing in the conductor coils 52, 54, which in turn causes a magnetic field with concentric field lines around the inner conductor coil 52. The electric and magnetic field components contribute to an axial electromagnetic wave traveling along the implantable medical lead 1.

The direction of the wave propagation depends on the direction of the implantable medical lead 1 relatively the MRI scanner. The wave could either travel towards the proximal end 3, at which a huge capacitance is generally placed (feedthrough capacitor of the sensing input, in the order of 3 nF). The RF wave will be totally reflected towards the distal end 2. At the distal end 2, the coaxial structure ends abruptly, and the wave is no longer able to continue. Instead, the currents in the inner and outer conductor coils 52, 54 will continue to flow into the tissue. The tissue can be modeled as a resistive load in series with a capacitive load. At this high frequency the tissue can be regarded as pure resistive, providing good matching between the characteristic impedance of the lead body and the impedance of the tissue. This means that a substantial part of the wave energy will be deposited in the tissue in the vicinity of the lead tip causing heat dissipation and subsequently temperature rise. The degree of the temperature rise depends on the amount of heat dissipation which in turn depends on the current flowing into the tissue, and the heat capacitivity of the tissue. The same theory will apply if the wave travels towards the distal end 2. In this case the wave will travel directly to the distal end 2 depositing its energy to the tissue.

The electric and magnetic field components of the incident RF wave have different impact on the RF energy absorption of the implantable medical lead 1. If the implantable medical lead 1 is configured straight, then the electric component will have higher impact on the energy absorption, whereas if the implantable medical lead 1 is coiled, then the magnetic component will dominate. The inner conductor coil 52 is exposed to considerably less incident RF wave. The portions of the incident wave that reach the inner conductor coil 52 will lose their phase due to scattering and are accordingly not able to propagate. They only contribute to some local heating and radiation. The pulsed gradient field has no impact on the heating due to its low frequency nature. This has also been verified experimentally.

One theoretical solution that allows reduction of the undesired heating would be to insert a capacitor close to the distal end 2 to drain the tip current. However, this turns out to be a very cumbersome mechanical operation. The embodiments instead take advantage of the impedance transformation or impedance mirroring property of a transmission line to mirror a capacitance placed at distance D from the distal end 2. This will have the same effect as placing a capacitor at the distal end 2, i.e. achieving a capacitance for draining the current before it reaches the distal end 2, and hence reducing the tip current and subsequently the heating.

In the MRI RF spectrum the implantable medical lead 1 will act both as an effective antenna due to its physical length, which is close to the effective wavelength of the RF wavelength in tissue, and as a transmission line due to its coaxial structure. A transmission line exhibits several interesting microwave properties which are utilized according to the embodiments. Firstly, it becomes a waveguide. If RF energy is absorbed by the transmission line in some way, a wave will be created in the transmission line. Secondly, if the ends of the transmission line are shorted or open, this wave will be reflected at the ends creating a standing wave. The energy will be confined within the transmission line. In practice, there will be some ohmic loss due to the resistance in the conductor coils 52, 54 and the imaginary part of the dielectric constant of the inner insulating tubing 51. Thirdly, a coaxial structure is characterized by a characteristic impedance. If one of the ends or both ends are terminated with real load, which means impedance matching between the transmission line and the load, parts of the wave energy will be deposited on the real load. The amount of the transferred energy depends on the degree of matching. Fourthly, if any load is placed at a certain position between the inner and outer conductor coil 52, 54, the impedance of that load will appear at a distance corresponding to half a wavelength or multiples of half a wavelength from the load. For example, if a capacitor 55 is placed at a certain position of the coaxial structure between the inner and outer conductor coils 52, 54, the capacitance will also appear at a distance of half a wavelength (or multiples thereof) from the capacitor 55. It is said that the capacitor 55 is "mirrored" to a position at half a wavelength from the physical capacitor 55. The embodiments take advantage of these properties to reduce the lead tip heating in MRI environment.

The distance D is therefore selected to take advantage of the impedance transformation property of the coaxial structure of the implantable medical lead 1. Hence, if the capacitor 55 is arranged at a position 6 relative to the distal end 2 of the implantable medical lead 1 so that the distance D between this position 6 and the tip or distal end 2 is defined based on the magnetic field strength of the MRI system, the impedance of the capacitor 55 will be mirrored to the distal end 2. This corresponds to arranging a "virtual" capacitor between the first electrode 22 and the second electrode 24 in connection with the distal end 2. The impedance of the capacitor 55 is thereby mirrored to the distal end 2 to provide a low impedance between the first electrode 22 and the second electrode 24. This impedance will drain the current induced by the MRI system between the first electrode 22 and the second electrode 24.

Thus, instead of physically arranging a capacitor of low impedance between the first electrode 22 and the second electrode 24 in connection with the distal end 2 of the implantable medical lead 1, the embodiments take advantage of the impedance transformation properties. It is generally very difficult to arrange a capacitor in the most distal part of the implantable medical lead 1 due to the different lead components that are needed therein in order to achieve the correct pacing and sensing functions by the implantable medical lead 1. The embodiments thereby arrange the capacitor 55 remotely from the distal end 2 and instead use the impedance transformation to mirror the capacitor 55 and its impedance towards the distal end 2. The result will basically be the same as having a real capacitor arranged between the two electrodes 22, 24. Thus, the capacitor 55 will, due to this impedance transformation, mirror its impedance between the two electrodes 22, 24 to thereby drain the MRI-induced current between the electrodes 22, 24 inside the implantable medical lead 1. This effectively reduces the current to the external tissue and thereby also the heating, which the external tissue is exposed to, will be effectively reduced.

The position 6 of the capacitor 55 is preferably defined based on the magnetic field strength of the MRI system so that the capacitor 55 is positioned at a distance corresponding to $$\frac{\lambda}{2}$$

or a multiple of $$\frac{\lambda}{2},$$

where $\lambda$ is me wavelength of the RF field or pulses of the MRI system in the animal tissue. In such a case, the impedance transformation will mirror the capacitor 55 and its impedance to a correct position in connection with the distal end 2.

In a particular embodiment, the distance D is defined based on:

$$k\frac{c}{2Y\gamma\sqrt{\varepsilon}} \quad (1)$$

where k is a positive integer, c is the speed of light in vacuum, Y is the magnetic field strength of the MRI system in Tesla, $\gamma$ is 42.58 MHz/Tesla and $\in$ is the real part of the dielectric constant of the tissue where the implantable medical lead 1 is to be implanted. In such a case, the distance D will correspond to $$\frac{\lambda}{2}$$

or a multiple of $$\frac{\lambda}{2}.$$

Hence and disregarding the positive integer, the distance D from the distal end 2 is inversely proportional to the magnetic field strength of the MRI system. For instance, with a 1.5 T MRI scanner or system the distance D is about $$k\frac{2.35}{\sqrt{\varepsilon}}$$

meter. The dielectric constant of the tissue/tissues where the implantable medical device 1 is implanted can be approximated by the dielectric constant of water at body temperature, i.e. about 80-81. In such a case, the distance D can be approximated as 0.26 k meter. A traditional implantable medical lead 1 is about half a meter long. With the integer k=1, this would correspond to arranging the capacitor 55 at about 26 cm from the distal end 2 or close to the middle point of the implantable medical lead 1.

If the same implantable medical lead 1 is instead used in a 3 T MRI scanner or system the distance D can be approximated as 0.13 k meter. With k=1 this would correspond to arranging the capacitor 55 about 13 cm from the distal end 2 and with k=2 the capacitor 55 is instead arranged about 26 cm from the distal end 2. If the implantable medical lead 1 is designed to be solely used with a 3 T MRI system it is acceptable to provide the capacitor 55 about 13 cm from the distal end 2 in order to enable a mirroring of the impedance of the capacitor 55 to the distal end 2 to drain any induced current between the two electrodes 22, 24. However, such an implantable medical lead 1 could still run into problems with induced currents and tissue heating when used in a 1.5 T MRI system. It is therefore preferred to instead use a distance D of about 26 cm to thereby get an implantable medical lead 1 that is compatible with both 1.5 T and 3 T MRI systems.

This means that when the implantable medical lead 1 is to be compatible with multiple MRI systems of different magnetic field strengths, the parameter Y is then the magnetic field strength of the MRI system having the smallest magnetic field strength. The parameter k is then preferably one or at least selected to be a positive integer that results in a distance D that does not exceed the length of the implantable medical lead 1.

In a particular embodiment, the parameter $$k = \frac{Y}{1.5}.$$

This implies that the implantable medical lead 1 can be used in connection with MRI systems of both 1.5 T and 3 T.

Figure 3:
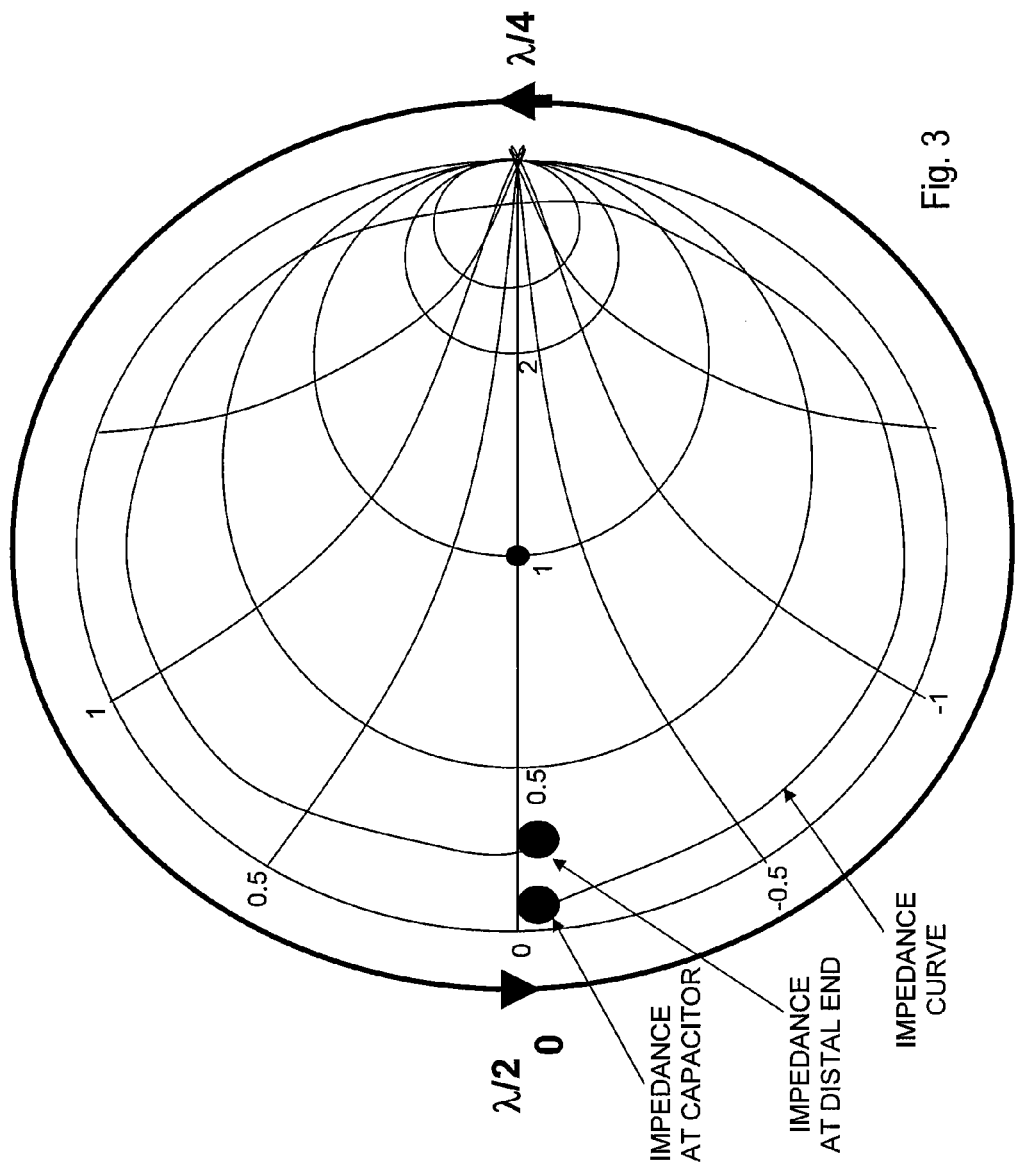
FIG. 3 is a Smith chart illustrating the impedance transformation achieved in an MRI-compatible implantable medical lead according to an embodiment.

FIG. 3 is a Smith chart illustrating the impedance transformation achieved according to the embodiments. The leftmost dot in the Smith chart corresponds to the impedance of the capacitor 55. When moving away from the capacitor 55 towards the distal end 2 of the implantable medical lead 1, the impedance is changing along the marked curve until the distal end 2. The impedance at the distal end 2 is represented by the rightmost dot. If the implantable medical lead 1 would be lossless this dot would coincide with the dot representing the impedance at the capacitor 55. However, since the implantable medical lead 1 does have some internal losses, the dot representing the impedance at the distal end 2 is slightly closer to the center of the Smith chart. This applies to a 1.5 T MRI scanner. For a 3 T MRI scanner and using k=2 in equation 1, the distance D between the capacitor 55 and the distal end becomes 1λ and one additional turn (not shown) in the Smith chart is traveled. However, the impedance still ends up in the vicinity of the rightmost dot in FIG. 3. Hence, the impedance transformation implies that a low impedance is mirrored between the two distal electrodes 22, 24 to thereby drain an induced current inside the implantable medical lead 1.

Circuit simulations have been conducted and the results indicate that the capacitor 55 preferably has a capacitance of at least 50 pF. In such a case, the current reduction for a standard implantable medical lead with an outer coil inductance of about 2-3 pH and an inner coil inductance of 1-2 pH is about three times, which means a temperature reduction by a factor of nine. This thereby significantly reduces any tissue heating and brings such induced heating to acceptable levels. In a particular embodiment the capacitance is preferably in the range of 50 pF to 100 pF. This upper limit is mainly dictated by practical implementation limits.

Figure 4:
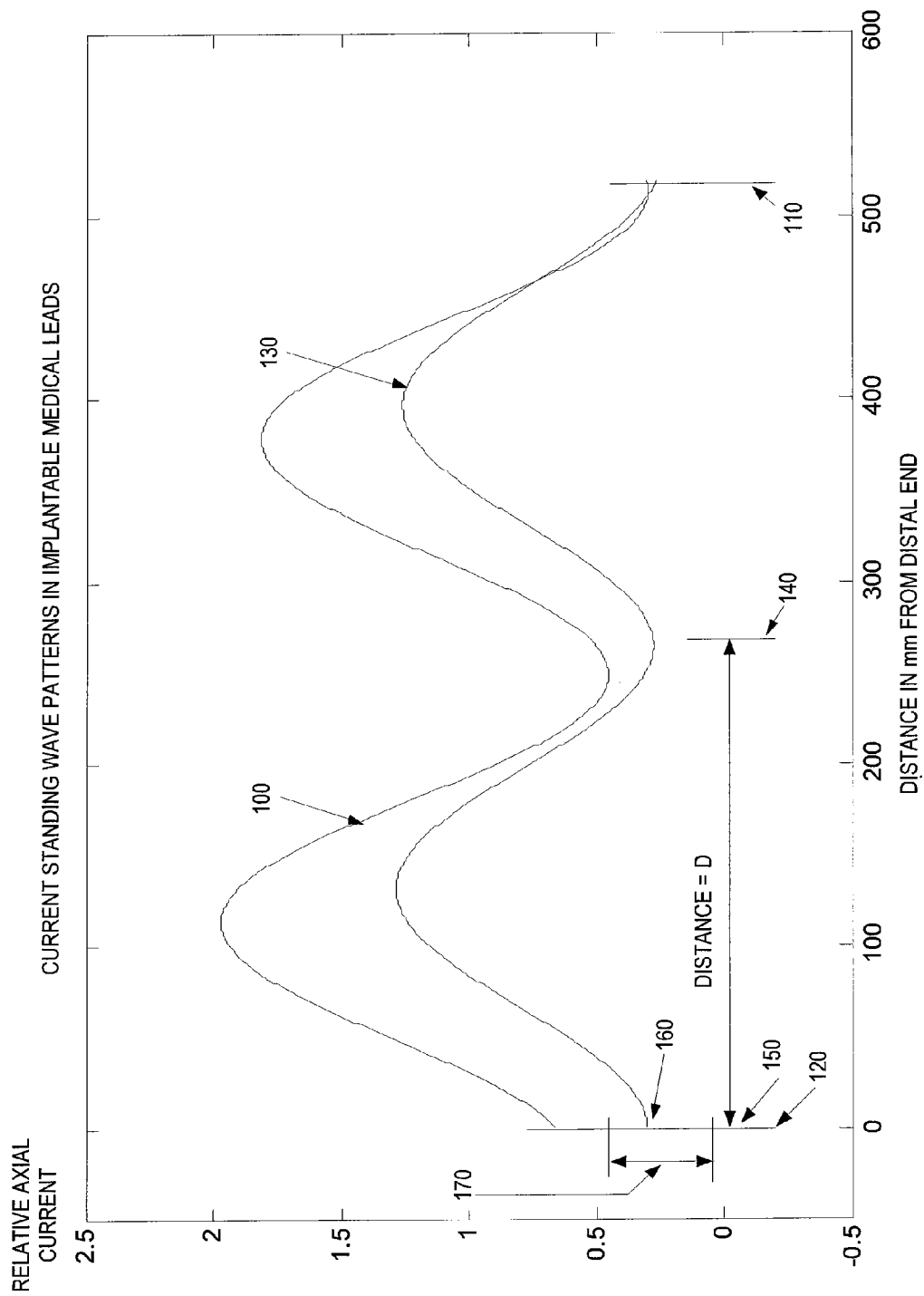
FIG. 4 is a diagram illustrating current standing wave patterns in implantable medical leads.

FIG. 4 schematically illustrates the concept of current standing wave patterns in implantable medical leads inducible in MRI systems. The upper curve 100 represents an unmodified standard implantable medical lead with a length of approximately one wavelength. The incident RF wave causes, as previously explained, an axial wave along the lead. The wave is losslessly reflected at the proximal end due to the huge feed-through capacitor (IMD interface at proximal end is marked as 110 in FIG. 4). At the distal end, the tissue makes up a resistive load which provides an impedance matching, not perfect, but sufficient to allow a substantial current to flow into the tissue (tissue interface at distal end is marked as 120 in FIG. 4). Due to the fact that the length is not exactly one wavelength, the feed-through capacitor is not exactly mirrored at the distal end. Thus, the distal end current is not at its minimum. The two mechanisms together contribute to a relatively high distal end current.

The lower curve 130 represents an implantable medical lead 1 according to an embodiment with a capacitor placed at distance D from the distal end, marked as reference number 140 in FIG. 4. This provides a current minimum at the distal end since the capacitor is placed at half a wavelength from the distal end. At the position of the capacitor, the leakage current between the inner and outer conductor coils will be at its maximum, and the same is true at the position of the mirrored capacitance, marked as 150 in FIG. 4. Since the leakage currents are at their maximum, the currents flowing along the implantable medical lead 1 will be at minimum at these positions as shown by reference number 160 in FIG. 4. The overall current pattern is also lower due to the fact that the mirrored capacitance provides a mismatch between the implantable medical lead and the tissue, and accordingly a lower distal end current. The three mechanisms together (guaranteed minimum, maximum leakage current and mismatch) contribute to the low distal end current, marked as reference number 170 in FIG. 4. These mechanisms are clearly illustrated in FIG. 4.

It is not necessary for achieving the technical effect in terms of impedance mirroring and current drainage that the capacitor 55 is positioned at a distance exactly equal to a value derived from equation 1 above. Thus, sufficient technical effect is still achieved if the capacitor 55 is at least arranged at a close distance from the position 6 corresponding to the distance D from the distal end 2. This close distance typically corresponds to one or a few centimeters, such as at most 2 cm, preferably no more than 1 cm. Thus, a distance D of about 26 cm could then correspond to 26±2 cm, preferably 26±1 cm.

In a more detailed approach the transformed impedance $x_C$ of the capacitor 55 can be calculated for various distances D according to below:

$$x_C = \frac{1}{2\pi f C},$$

wherein f=Yγ is the frequency of the RF field of the MRI system and C is the capacitance of the capacitor 55. If the MRI system is a 1.5 T MRI system and the capacitance is 50 pF, the impedance will be about 50Ω. The characteristic impedance ($z_0$) of the implantable medical lead 1 is approximately 100Ω. Normalizing the transformed impedance $$\frac{x_C}{z_0}$$

gives about 0.5. With reference to the Smith chart of FIG. 3, if the normalized transformed impedance is 0.5 find the point corresponding to the distance D of 26 cm and then move towards or from the tip to obtain the following normalized value for the transformed impedance for a capacitor 55 of 50 pF and for 100 pF (the latter being calculated in the same way as for C=50 pF).

TABLE 1

Normalized transformed impedance of capacitance for 1.5 T

| Length (cm) | Normalized transformed impedance (C = 50 pF) | Normalized transformed impedance (C = 100 pF) |
|---|---|---|
| 24 | 0.22 | 0.02 |
| 25 | 0.35 | 0.14 |
| 26 | 0.5 | 0.25 |
| 27 | 0.67 | 0.38 |
| 28 | 0.85 | 0.55 |

The same calculations have also been conducted for a 3 T MRI system and are presented in Table 2.

TABLE 2

Normalized transformed impedance of capacitance for 3 T

| Length (cm) | Normalized transformed impedance (C = 50 pF) | Normalized transformed impedance (C = 100 pF) |
|---|---|---|
| 24 | 0.02 | — |
| 25 | 0.14 | 0.03 |
| 26 | 0.25 | 0.13 |
| 27 | 0.38 | 0.25 |
| 28 | 0.55 | 0.38 |

Normalized impedances under 0.5 are very good and normalized impedances up to 1 are acceptable. The normalized impedance should, though, not be in or near the inductive region. Thus, it is clear from Table 1 and Table 2 that the distance D is preferably selected to be 26±2 cm and more preferably 26±1 cm in this example.

In a particular embodiment, the distance $$D = k\frac{c}{2Y\gamma\sqrt{\varepsilon}} \pm \zeta,$$

where $\zeta$ is an acceptable distance marginal, which can be obtained as described above and disclosed in Table 1 and Table 2. In an embodiment this distance marginal is zero giving $$D = k\frac{c}{2Y\gamma\sqrt{\varepsilon}}.$$

An important advantage of the embodiments is that the heating reduction achieved is independent of the properties of the implantable medical lead 1 between the capacitor 55 and the proximal end 3. This is possible since this portion of the implantable medical lead 1 is shielded off by the capacitor 55. In other words, the heating reduction is independent of whether this portion of the implantable medical lead 1 is kept straight or wrapped around the IMD 5 and independent of whether the proximal end 3 is connected to the IMD 5 or left open, i.e. abandoned in the subject body.

The capacitor 55 of the implantable medical lead 1 at the defined distance D from the distal end 2 can be implemented according to various embodiments. FIG. 5 is a cross-sectional view of a portion of an implantable medical lead 1 according to an embodiment. FIG. 5 clearly shows the coaxial arrangement of the inner conductor 52, the inner insulating tubing 51 and the outer conductor 54 to form the coaxial conductor assembly 50. In this embodiment, the capacitor 55 is implemented by increasing the dielectric constant of a portion 53 of the inner insulating tubing 51 provided between the inner and outer conductors 52, 54. This increase in dielectric constant is preferably obtained by doping the portion 53 of the inner insulating tubing 51 with at least one doping material 60 having a higher dielectric constant than the electrically insulating material of the insulating tubing 51.

There are several doping materials that can be used to achieve this increase in dielectric constant. In a particular embodiment, the at least one doping material is selected among non-ferromagnetic perovskite-type of materials. Non-limiting, but preferred, examples of non-ferromagnetic perovskite-type materials include $BaTiO_3$, $CaCu_3Ti_4O_{12}$, $SrTiO_3$, $CaTiO_3$ and $Ba_xSr_{1-x}TiO_3$. Suitable materials that can be used according to the embodiments also include non-ferromagnetic but ferroelectric perovskite-type materials, such as $BaTiO_3$, $BaCu_{1/3}Nb_{2/3}O_3$, $(Na_{0.5}Bi_{0.5})_{1-x}(Ba_xTiO_3$, $Ba_{1-x}(La_{0.5}Na_{0.5})_xTiO_3$, $Ba_2Bi_4Ti_5O_{18}$, $Ba_xSr_{1-x}TiO_3$, $CaCu_3Ti_4O_{12}$ and $SrBi_2Ta_2O_9$. For the doping materials listed above $0 \leq x \leq 1$. In some applications, ferroelectric perovskite-type materials could be preferred since they generally lead to an increased dielectric constant when exposed to an electric field, which occurs when the implantable medical lead 1 is exposed to the RF field from the MRI system. Other doping materials that can be used include carbon black and titanium oxide. These materials can effectively be doped into the material of the insulating tubing 51, which advantageously can be made of silicone, polyurethane, a copolymer of polyurethane and silicone, such as Optim™, and other electrically insulating polymer materials.

The length L of the doped portion 53 of the inner insulating tubing 51 is preferably selected to prevent or at least reduce the risk of any microwave effects which could affect the characteristic impedance of the implantable medical lead 1 between the capacitor 55 and the distal end 2. The risk for such microwave effects is significantly reduced if the length L of the doped portion 53 does not exceed $$\frac{\lambda}{10},$$

wherein $\lambda$ is the wavelength of the RF field of the MRI system in animal tissue (corresponds to $$\frac{\lambda_0}{\sqrt{\varepsilon}},$$

where $\lambda$ is the wavelength in air and $\in$ is the real part of the dielectric constant of the animal tissue where the implantable medical lead 1 is to be implanted).

If the capacitance of the implantable medical lead 1 having a length around $\lambda$ is about 100 pF (typically the case for standard implantable medical leads and $\lambda$ is the wavelength of the RF field of a 1.5 T MRI system), the capacitance of a portion having length L would be $$\frac{100}{10} \approx 10 \text{ pF}.$$

If the doping of this portion 53 would result in a capacitance of 50-100 pF, the capacitance would need to be increased at least 5 times, such as 5-10 times. This can be achieved by increasing the dielectric constant of this portion 53 at least 5 times, such as about 5-10 times. A typical insulating material of the insulating tubing 51 has a dielectric constant of about 3. This implies that the doping should preferably increase the dielectric constant to about 15-30, such as at least 20.

Figure 6:
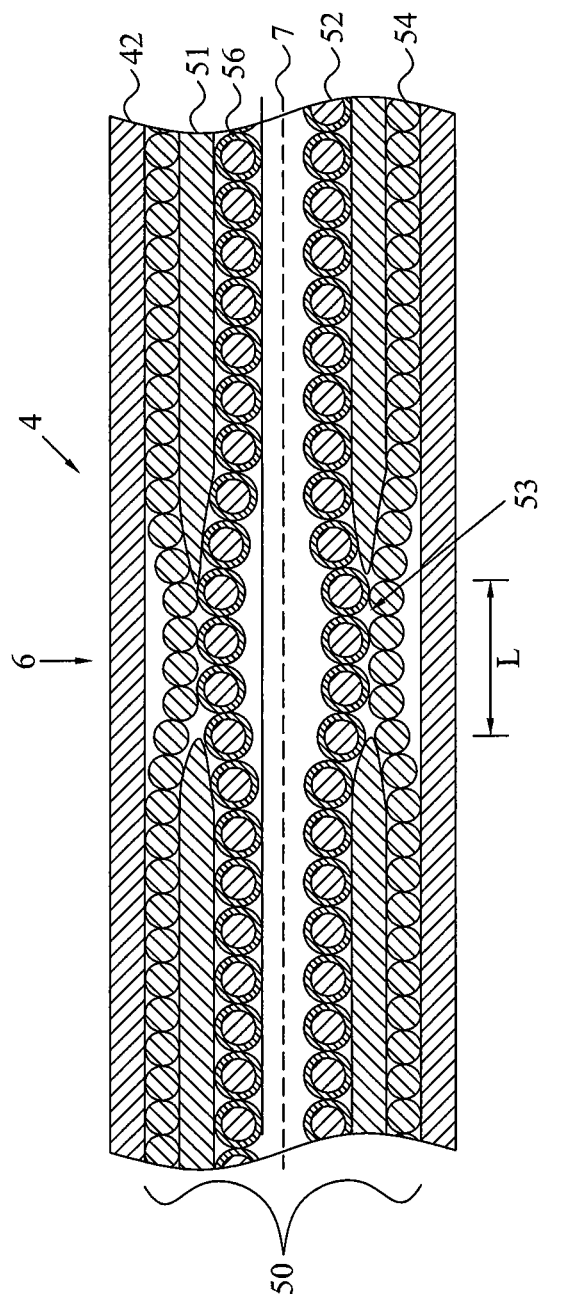
FIG. 6 is a cross-sectional view of portion of the lead body of an MRI-compatible implantable medical lead according to another embodiment.

In an alternative embodiment, capacitor can be implemented by removing a portion 53 of the inner insulating tubing 51 as is illustrated in FIG. 6. In this embodiment, at least one of the inner conductor 52 and the outer conductor 54 is in the form of a conductor coil surrounded by an insulating layer 56 around the electrically conducting wire(s). In a particular embodiment both the inner and outer conductors 52, 54 are in the form of conductor coils surrounded by respective insulating layers 56. The removal of a portion 53 of the inner insulating tubing 51 implies that the two conductors 52, 54 are brought together and the distance therebetween is decreased. This corresponds to increasing the capacitance of this portion 53 of the implantable medical lead 1 and effectively forms a capacitor. The length L of this relevant portion 53 where the inner insulating tubing 51 has been removed should preferably not exceed $$\frac{\lambda}{10}$$

in order to reduce the risk of any microwave effects.

In an alternative but less effective embodiment it could be possible to implement the capacitor 55 by not removing the inner insulating tubing 51 completely for a portion 53 of the lead length but instead reduce the thickness of the inner insulating tubing 51 for this portion 53. In such a case, it might not be necessary to provide separate insulating layers 56 around the inner and/or outer conductor coil 52, 54.

The doped portion 53 of the inner insulating tubing 51 in FIG. 5 and the omitted portion 53 of the inner insulating tubing 51 in FIG. 6 is positioned at the distance D from the distal end 2. This means that the site 6 positioned at the distance D from the distal end 2 preferably falls within the lengths L of the doped or omitted portion 53. In a preferred embodiment, the site 6 is preferably positioned in the center of or at least close to the center of the length L. In such a case, the impedance transformation will mirror the created (due to doping or insulation removal) low impedance of the capacitor 55 to the correct position at the distal end 2 to achieve the current drainage and tissue heating reduction.

A major advantage of the embodiments is that the beneficial effects in terms of current drainage and tissue heating reductions are achieved using a single capacitor 55 arranged between the inner conductor 52 and the outer conductor 54 at the defined distance D from the distal end 2. There is therefore, due to defining this distance D based on the magnetic field strength of the MRI system, no need to have multiple added MRI/RF-compensating structures along the whole length of the implantable medical lead 1. Hence, the cost and complexity of manufacturing the implantable medical lead 1 of the embodiments can be kept low as compared to the MRI-compatible implantable medical leads according to the prior art.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. An implantable medical lead compatible with a Magnetic Resonance Imaging (MRI) system comprising:
   a first electrode and a second electrode arranged in connection with a distal end of said implantable medical lead;
   a connector having a first electrode terminal and a second electrode terminal, the connector being configured to be mechanically and electrically coupled to an implantable medical device;
   a coaxial conductor assembly having an inner conductor electrically coupled to said first electrode and said first electrode terminal, an outer conductor electrically coupled to said second electrode and said second electrode terminal and an inner insulating tubing arranged between said inner conductor and said outer conductor for electrically isolating said inner conductor from said outer conductor,
   a capacitor arranged between said inner conductor and said outer conductor at a distance D from said distal end defined based on a magnetic field strength of said MRI system, wherein said distance D is defined based on said magnetic field strength so that an impedance of said capacitor is mirrored to said distal end to provide an impedance between said first electrode and said second electrode that drains a current, induced by said MRI system, between said first electrode and said second electrode.

2. The implantable medical lead of claim 1 wherein said distance D is defined based on $$k\frac{c}{2Y\gamma\sqrt{\varepsilon}},$$

where k is a positive integer, c is the speed of light in vacuum, Y is the magnetic field strength of said MRI system in Tesla, γ is 42.58 MHz/Tesla and ∈ is the real part of the dielectric constant of the tissue where said implantable medical lead (1) is to be implanted.

3. The implantable medical lead of claim 2 wherein $$k = \frac{Y}{1.5}.$$

4. The implantable medical lead of claim 2 wherein Y is the magnetic field strength in Tesla of the MRI system having the smallest magnetic field strength of a set of multiple MRI systems with which said implantable medical lead is compatible.

5. The implantable medical lead of claim 1 wherein said capacitor has a capacitance in the range of 50 pF to 100 pF.

6. The implantable medical lead of claim 1 wherein said capacitor is formed by doping a portion, positioned at said distance D from said distal end, of said inner insulating tubing with at least one doping material having a higher dielectric constant than the material of said inner insulating tubing.

7. The implantable medical lead of claim 6 wherein a length L of said doped portion along a longitudinal axis of said implantable medical lead does not exceed $$\frac{\lambda}{10},$$

wherein λ is a wavelength of a radio frequency field of said MRI system in the tissue where said implantable medical lead is to be implanted.

8. The implantable medical lead of claim 6 wherein said at least one doping material has a dielectric constant that is 5 to 10 times greater than said dielectric constant of said material of said inner insulating tubing.

9. The implantable medical lead of claim 6 wherein said at least one doping material is selected among perovskite-type of materials, preferably selected among the group consisting of $BaTiO_3$, $CaCu_3Ti_4O_{12}$, $SrTiO_3$, $CaTiO_3$ and $Ba_xSr_{1-x}TiO_3$.

10. The implantable medical lead of claim 6 wherein said at least one doping material is selected among ferroelectric perovskite-type of materials, preferably selected among the group consisting of $BaTiO_3$, $BaCu_{1/3}Nb_{2/3}O_3$, $(Na_{0.5}Bi_{0.5})_{1-x}Ba_xTiO_3$, $Ba_{1-x}(La_{0.5}Na_{0.5})_xTiO_3$, $Ba_2Bi_4Ti_5O_{18}$, $Ba_xSr_{1-x}TiO_3$, $CaCu_3Ti_4O_{12}$ and $SrBi_2Ta_2O_9$.

11. The implantable medical lead of claim 1 wherein at least one of said inner conductor and said outer conductor is in the form of a conductor coil surrounded by an insulating layer, wherein said capacitor is formed by removing a portion of said inner insulating tubing at said distance D from said distal end.

12. The implantable medical lead of claim 11 wherein a length L of said portion along a longitudinal axis of said implantable medical lead does not exceed $$\frac{\lambda}{10},$$

wherein λ is a wavelength of a radio frequency field of said MRI system in the tissue where said implantable medical lead is to be implanted.

13. The implantable medical lead of claim 1 wherein said coaxial conductor assembly comprises a single capacitor arranged between said inner conductor and said outer conductor at said distance D from said distal end.

14. An implantable medical lead compatible with a Magnetic Resonance Imaging (MRI) system comprising:
  a first electrode and a second electrode arranged in connection with a distal end of said implantable medical lead;
  a coaxial conductor assembly having an inner conductor electrically coupled to said first electrode, an outer conductor electrically coupled to said second electrode and an inner insulating tubing arranged between said inner conductor and said outer conductor for electrically isolating said inner conductor from said outer conductor,
  a capacitor arranged between said inner conductor and said outer conductor at a distance D from said distal end defined based on a magnetic field strength of said MRI system so that an impedance of said capacitor is mirrored to said distal end to provide an impedance between said first electrode and said second electrode that drains a current, induced by said MRI system, between said first electrode and said second electrode;
  trending the sinus rate over time using sinus rate values satisfying the measurement conditions; and
  determining a preferred pacing therapy setting providing a lowest sinus rate based on a trend analysis of the sinus rate.

* * * * *